(12) United States Patent
Jung et al.

(10) Patent No.: US 9,486,554 B2
(45) Date of Patent: Nov. 8, 2016

(54) WOUND CARE COMPOSITIONS COMPRISING BORATE ($B_2O_3$) GLASS-BASED PARTICLES

(71) Applicant: The Curators of the University of Missouri, Columbia, MO (US)

(72) Inventors: Steven B. Jung, Rolla, MO (US); Delbert E. Day, Rolla, MO (US)

(73) Assignee: The Curators of the University of Missouri, Columbia, MO (US)

( * ) Notice: Subject to any disclaimer, the term of this patent is extended or adjusted under 35 U.S.C. 154(b) by 47 days.

(21) Appl. No.: 14/028,148

(22) Filed: Sep. 16, 2013

(65) Prior Publication Data

US 2014/0017320 A1 Jan. 16, 2014

Related U.S. Application Data

(63) Continuation of application No. 13/442,051, filed on Apr. 9, 2012, now Pat. No. 8,535,710, which is a continuation of application No. 12/683,244, filed on Jan. 6, 2010, now Pat. No. 8,173,154.

(51) Int. Cl.
*A61K 9/14* (2006.01)
*A61L 15/00* (2006.01)
(Continued)

(52) U.S. Cl.
CPC .......... *A61L 17/00* (2013.01); *A61F 13/00008* (2013.01); *A61F 13/00034* (2013.01); *A61K 33/16* (2013.01); *A61K 33/22* (2013.01); *A61K 33/26* (2013.01); *A61K 33/30* (2013.01);
(Continued)

(58) Field of Classification Search
CPC ....... A61L 15/18; A61L 15/42; A61L 17/00; A61F 13/00008; A61F 13/00034; A61F 13/069; A61F 2013/00829; A61F 2013/00936; A61K 33/16; A61K 33/26; A61K 33/30; A61K 33/32; A61K 33/34; A61K 33/38; A61K 33/22; A61K 9/0014; A61K 9/06
USPC ......... 514/769, 770; 606/228; 424/489, 445, 424/657
See application file for complete search history.

(56) References Cited

U.S. PATENT DOCUMENTS

| | | | |
|---|---|---|---|
| 2,156,316 A | 5/1939 | Slayter et al. | |
| 2,165,318 A | 7/1939 | Thomas et al. | |

(Continued)

FOREIGN PATENT DOCUMENTS

| | | |
|---|---|---|
| EP | 1716873 | 11/2006 |
| JP | H05-200104 A | 8/1993 |

(Continued)

OTHER PUBLICATIONS

Rahaman et al. (Preparation and bioactive characteristics of porous borate glass substrates, Advances in Bioceramics and Biocomposites: Ceramic Engineering and Science Proceedings, vol. 26, No. 6 (2005; pub. on line, Mar. 27, 2008), pp. 3-10, plus cover page (total 9 pages).*

(Continued)

*Primary Examiner* — Anna Pagonakis
*Assistant Examiner* — Miriam A Levin
(74) *Attorney, Agent, or Firm* — Senniger Powers LLP

(57) ABSTRACT

Glass-based angiogenic particles of a biocompatible material which comprises 40 to about 80 wt% borate ($B_2O_3$) intermixed into a carrier which is an ointment, cream, or surgical glue.

23 Claims, 8 Drawing Sheets

(51) Int. Cl.

| | | |
|---|---|---|
| *A61K 33/22* | (2006.01) | |
| *A61K 47/00* | (2006.01) | |
| *A61L 17/00* | (2006.01) | |
| *A61F 13/00* | (2006.01) | |
| *A61K 33/16* | (2006.01) | |
| *A61K 33/26* | (2006.01) | |
| *A61K 33/30* | (2006.01) | |
| *A61K 33/32* | (2006.01) | |
| *A61K 33/34* | (2006.01) | |
| *A61K 33/38* | (2006.01) | |
| *A61L 15/18* | (2006.01) | |
| *A61L 15/42* | (2006.01) | |
| *A61L 15/64* | (2006.01) | |
| *A61L 26/00* | (2006.01) | |
| *A61F 13/06* | (2006.01) | |
| *A61K 9/00* | (2006.01) | |
| *A61K 9/06* | (2006.01) | |

(52) U.S. Cl.
CPC .............. *A61K33/32* (2013.01); *A61K 33/34* (2013.01); *A61K 33/38* (2013.01); *A61L 15/18* (2013.01); *A61L 15/42* (2013.01); *A61L 15/425* (2013.01); *A61L 15/64* (2013.01); *A61L 26/0004* (2013.01); *A61L 26/0009* (2013.01); *A61L 26/0085* (2013.01); *A61F 13/069* (2013.01); *A61F 2013/00157* (2013.01); *A61F 2013/00221* (2013.01); *A61F 2013/00519* (2013.01); *A61F 2013/00829* (2013.01); *A61F 2013/00936* (2013.01); *A61K 9/0014* (2013.01); *A61K 9/06* (2013.01); *A61L 2400/12* (2013.01)

(56) References Cited

U.S. PATENT DOCUMENTS

| | | | |
|---|---|---|---|
| 2,430,740 | A | 11/1947 | Sharlpes |
| 3,622,445 | A | 11/1971 | Heidweiller |
| 4,842,620 | A | 6/1989 | Hammel et al. |
| 4,853,001 | A | 8/1989 | Hammel |
| 4,933,307 | A | 6/1990 | Marshall et al. |
| 5,179,152 | A | 1/1993 | Shimaoka et al. |
| 5,977,428 | A | 11/1999 | Bozigian et al. |
| 6,057,472 | A * | 5/2000 | Sailhan ................. C07C 253/30 558/381 |
| 6,143,318 | A | 11/2000 | Gilchrist et al. |
| 6,204,971 | B1 | 3/2001 | Morris et al. |
| 6,326,025 | B1 * | 12/2001 | Sigler ..................... A61L 24/04 424/444 |
| 6,447,805 | B1 | 9/2002 | Healy |
| 6,482,444 | B1 | 11/2002 | Bellantone et al. |
| 6,709,744 | B1 | 3/2004 | Day et al. |
| 6,756,060 | B1 | 6/2004 | Greenspan et al. |
| 7,166,549 | B2 | 1/2007 | Fechner et al. |
| 7,495,146 | B2 | 2/2009 | Crisp |
| 7,517,536 | B2 | 4/2009 | Ko |
| 7,605,298 | B2 | 10/2009 | Bechert et al. |
| 7,638,484 | B2 | 12/2009 | Braiman-Wiksman et al. |
| 7,709,027 | B2 | 5/2010 | Fechner et al. |
| 8,173,154 | B2 | 5/2012 | Jung et al. |
| 2004/0078077 | A1 | 4/2004 | Binette et al. |
| 2004/0166172 | A1 | 8/2004 | Rosati et al. |
| 2004/0170692 | A1 * | 9/2004 | Day ....................... A61K 33/42 424/489 |
| 2004/0253321 | A1 | 12/2004 | Fechner et al. |
| 2005/0065214 | A1 * | 3/2005 | Kronenthal ................... 514/557 |
| 2005/0169967 | A1 | 8/2005 | Gilchrist et al. |
| 2006/0062831 | A1 | 3/2006 | Meyer-Ingold et al. |
| 2006/0204738 | A1 | 9/2006 | Dubrow et al. |
| 2006/0233887 | A1 | 10/2006 | Day |
| 2007/0020320 | A1 | 1/2007 | David et al. |
| 2011/0014261 | A1 | 1/2011 | Day et al. |
| 2011/0165221 | A1 | 7/2011 | Jung et al. |

FOREIGN PATENT DOCUMENTS

| | | |
|---|---|---|
| WO | 80/02378 | 11/1980 |
| WO | 9854104 | 12/1998 |

OTHER PUBLICATIONS

Citation and source information for Rahaman article, [Retrieved from internet <URL: http://onlinelibrary.wiley.com/doi/10.1002/9780470291269.ch1/summary >], [downloaded Jun. 10, 2016], 3 pages.*

Durand et al., Angiogenic effects of ionic dissolution products released from a boron-doped 45S5 bioactive glass, Journal of Materials Chemistry B, 2015, 3, 1142-1148.*

Rahaman et al., (2005) Preparation and Bioactive Characteristics of Porous Borate Glass Substrates, in Advances in Bioceramics and Biocomposites: Ceramic Engineering and Science Proceedings, vol. 26. No. 6 (ed. M. Mizuno) (John Wiley and Sons), pp. 2-10.* citation and source information for Rahaman article [Retrieved from internet <URL: http://onlinelibrary.wiley.com/doi/10.1002/9780470291269.ch1/summary >] [Downloaded Jun. 10, 2016], 3 pages.*

Wang et al., Bone Morphogenic Protein (BMP) Signaling in Development and Human Diseases; Genes & Diseases, vol. 1, Issue 1 (Sep. 2014), pp. 87-105.*

"3M, Products—3M US Skin and Wound Care [Downloaded Jun. 4, 2011] [Retrieved from internet CURL:http://solutions.3m.com. wps/portal/3M/enUS/3MSWC/Skin-Wound-Care/Product/Directory/], (1 page)".

"Department Store, Wound Dressigs/Wound Supplies [Downloaded Jun. 4, 2011] [Retrieved from internet CURL: http://web.archive. orgweb/20081221003838/http://www.medicaldepartmentstore. com/Wound-Dressings-Supplies-2/81. htm >] (5pages) Medical Department Store, Composite Wound Dressings [Downloaded Jun. 4, 2011 [Retrieved frominternet CURL: http://ww. medicaldepartmentstore.com/Composite-Wound-Dressings-s/291/ htm >], (3 pages) (total pages=8, 5from above portion of reference, and 3 pages from this portion)".

Jung, Steven, "Conversion Kinetics of Silicate, Borosilicate, and Borate Bioactive Glasses to Hydroxyapatite", Physics and Chemistry of Glasses—European Journal of Glass Science and Technology Part B, Apr. 2009, vol. 50, No. 2, pp. 85-88.

Liang, Wen et al., "Bioactive Borate Glass Scaffold for Bone Tissue Engineering", Journal of Non-Crystalline Solids, Journal of Non-Crystalline Solids, vol. 354, Issues 15-16, Mar. 15, 2008, pp. 1690-1696.

Liang, Wen, "Bioactive Comparison of a Borate, Phosphate and Silicate Glass", Journal of Materials Research, vol. 21, Issue 1, 2005, pp. 125-131.

Ning, Jia et al., "Synthesis and in Vitro Bioactivity of a Borate-Based Bioglass", Materials Letters, vol. 61, Issue 30, Dec. 2007, pp. 5223-5226.

Waser et al., Chem One, McGraw Hill, Inc. (1976), 5 pages.

Wikipedia, Glass Wool [Downloaded Jun. 4, 2011] [Retrieved from Internet CURL: http://en.wikipedia.org/wiki/Glass~wool> ], (1 page).

Yao, Aihua et al., "In Vitro Bioactive Characteristics of Borate-Based Glasses with Controllable Degradation Behavior", Journal of the American Ceramic Society, vol. 90 Issue 1, Nov. 7, 2006, pp. 303-306.

Medline Industries, Inc., Sterile Cotton Rolls ([Downloaded Nov. 29, 2012] [Retrieved from internet <URL: http://www.medline. com/product/Sterile-Cotton-Rolls/Cotton-Rolls/Z05-PF03-654 >]), 1 page.

Kunimoto, Brian. "Management and Prevention of Venous Leg Ulcers: A Literature Guided Approach", Ostomy/Wound Management, Jun. 2001, vol. 47, Issue 6, pp. 36-49.

Singhal et al., "Options for Nonsurgical Debridement of Necrotic Wounds", Advances in Skin & Wound Care: The Journal for Prevention and Healing, Mar./Apr. 2001, vol. 14, No. 2, p. 96, <http://endoflifecare.tripod.com/imbeddedlinks/id3.html>.

(56) References Cited

OTHER PUBLICATIONS

Dressing Selection Guide by Wound Condition, 2008, 2 pages, <http://www.mhcwoundcare.com/education_resources/Wound_Dressing_Selection_Guide.pdf>.

Shai et al., "Scaled Healing Assessment Index: a novel method for measuring the degree of wound bed preparation", Skin Research and Technology, Aug. 2007, vol. 13, Issue 3, pp. 227-235.

Bryant et al., "Acute and Chronic Wounds: Current Management Concepts", Feb. 2011, Fourth Edition, Chapter 17, p. 279-287.

Wray, Peter, "Cotton Candy' that heals? Borate glass nanofibers look promising", American Ceramic Society Bulletin, vol. 90, No. 4, May 11, 2011, 5 pages, <http://ceramics.org/wp-content/uploads/2011/04/bulletin-may11-cover.pdf>.

Laplaud et al., "Wound debridement: Comparative reliability of three methods for measuring fibrin percentage in chronic wounds", Wound Repair and Regeneration, 2010, No. 18, pp. 13-20.

Abstract JPH05-200104 A, 2 pages.

Supplementary European Search Report, EP Application No. 11732137.2, dated Aug. 2, 2016, 10 pages.

\* cited by examiner

93B3 glass; Fiber diameter from ~0.3μm to ~2μm.

CONTROL MESH

Day 0

CONTROL MESH

Day 4

CONTROL MESH

Day 7

Day 11

Day 15

Day 18

Day 22

Day 0

Day 4

Day 7

Day 11

200x

400x

200x

200x

WOUND CARE COMPOSITIONS COMPRISING BORATE ($B_2O_3$) GLASS-BASED PARTICLES

REFERENCE TO RELATED APPLICATION

This is a continuation of U.S. application Ser. No. 13/442,051, filed Apr. 9, 2012, now U.S. Pat. No. 8,535,710; which is a continuation of U.S. application Ser. No. 12/683,244, filed Jan. 6, 2010, now U.S. Pat. No. 8,173,154; the entire disclosures of which are incorporated by reference.

STATEMENT OF GOVERNMENT INTEREST

This invention was made with Government support under Department of the Army contract W81XWH-08-1-7065. The Government may have certain rights in the invention.

FIELD OF THE INVENTION

This invention relates to biocompatible dressings for care of open wounds such as lacerations, diabetic ulcers, bed sores, and burns.

BACKGROUND OF THE INVENTION

As noted in U.S. Pat. No. 7,638,484, (i) inflammation; (ii) fibroblast proliferation; (iii) blood vessel proliferation; (iv) connective tissue synthesis; (v) epithelialization; and (vi) wound contraction, are among the processes occurring during healing of open cutaneous. Various factors including malnutrition, infection, and pharmacological agents can affect the healing process.

U.S. Pat. No. 7,605,298 discloses a wound covering containing Ag, Cu, and/or Zn as an antimicrobially active substance bonded to the surface of a matrix. The covering includes a first layer formed by an absorbent matrix and an antimicrobially active substance, the substance being present chemically or physically bonded to one surface of the matrix. The surface of the matrix including the substance is coated with a hydrophilic polymer. The matrix contains fibers and can consist of a nonwoven material, of gauze, of a foam material, or of another soft absorbent material. A foam material is stated to have the advantage that it can bind material discharging from the wound and thereby can be kept remote from the wound, so that it does not interfere with the healing process. The matrix can contain at least one fiber or be formed from at least one fiber.

U.S. Pat. No. 7,517,536 discloses a wound dressing comprising a flexible base layer and an antimicrobial material, wherein the antimicrobial material comprises an activated carbon-carried noble metal. The activated carbon is selected from among an activated carbon powder, an activated carbon particle, and an activated carbon fiber. The noble metal is selected from the group consisting of silver, gold, palladium, platinum, copper, and zinc.

U.S. Pat. No. 7,495,146 discloses a wound dressing employing silver compounds and copper compounds in particles suspended in a fluid soluble material to establish electrochemical potential adjacent a healing wound.

U.S. Pat. No. 5,977,428 discloses an absorbent dressing comprising a copper-containing compound or complex as a micronutrient and a plurality of absorbent dried hydrogel particles sealed within a porous container, wherein the porous container is non-adherent to the wound. The absorbent hydrogel particles, after absorbing the exudate, remain sealed within the porous container.

U.S. Pat. No. 7,166,549 discloses grinding silicate glasses ribbons into antimicrobial, anti-inflammatory, wound-healing glass powders which may be added as a foodstuff supplement, in cosmetic production, antiperspirant production, in medicinal products, plastics and polymers, sanitary paper, dyes, and lacquers as well as plaster and purification means.

Patent application publication WO 80/02378 discloses a carrier manufactured from an absorbable plastic, ethylene/vinyl acetate, collagen, or albumin material for promoting vascularization and endothelial activity in mammals. The carrier is in the form of a tube, sheet, thread, or net, and can, for example, be laid over skin ulcers.

There is a continuing need for new approaches for accelerating the processes associated with healing open wounds such as but not limited to lacerations, diabetic ulcers, bed sores, and burns.

SUMMARY OF THE INVENTION

Briefly, therefore, the invention is directed to flexible dressing for wound care management comprising a three-dimensional compressible body of loose glass-based fibers; wherein the fibers comprise one or more glass-formers selected from the group consisting of $P_2O_5$, $SiO_2$, and $B_2O_3$; at least about 25 wt % of the fibers have a diameter between about 200 nm and about 4000 nm, and a length:width aspect ratio of at least about 10.

The invention is also directed to rigid dressing for wound care management comprising a three-dimensional body of bonded glass-based fibers; wherein the fibers comprise one or more glass-formers selected from the group consisting of $P_2O_5$, $SiO_2$, and $B_2O_3$; and at least about 25 wt % of the fibers have a diameter between about 200 nm and about 4000 nm, and a length:width aspect ratio of at least about 10.

In another aspect, the invention is directed to a dressing for wound care management comprising a three-dimensional compressible body of glass-based biocompatible material comprising one or more glass-formers selected from the group consisting of $P_2O_5$, $SiO_2$, and $B_2O_3$; and one or more trace elements selected from the group consisting of Ag, Cu, F, Fe, Mn, Mo, Ni, Sr, and Zn in a concentration between about 0.05 and 10 wt % per trace element chemically dissolved in the biocompatible material.

The invention is further directed to a biocompatible ointment or cream for wound care management comprising an ointment-based carrier; glass-based particles of a biocompatible material intermixed in the ointment-based carrier, wherein the glass-based particles comprise a glass-former selected from the group consisting of $P_2O_5$, $SiO_2$, $B_2O_3$; and one or more trace elements selected from the $B_2O_3$; and one or more trace elements selected from the group consisting of Ag, Cu, F, Fe, Mn, Mo, Ni, Sr, and Zn in a concentration between about 0.05 and 10 wt % per trace element chemically dissolved in the biocompatible material.

The invention is also directed to a biocompatible surgical glue for closing a wound, wherein the glue comprises an adhesive; glass-based particles of a biocompatible material intermixed in the adhesive, wherein the glass-based particles comprise a glass-former selected from the group consisting of $P_2O_5$, $SiO_2$, $B_2O_3$; and one or more trace elements selected from the group consisting of Ag, Cu, F, Fe, Mn, Mo, Ni, Sr, and Zn in a concentration between about 0.05 and 10 wt % per trace element chemically dissolved in the biocompatible material.

In a further embodiment the invention is a surgical suture for closing a wound wherein the suture comprises glass-based fibers of a biocompatible material comprising a glass-former selected from the group consisting of $P_2O_5$, $SiO_2$, $B_2O_3$; and one or more trace elements selected from the group consisting of Ag, Cu, F, Fe, Mn, Mo, Ni, Sr, and Zn in a concentration between about 0.05 and 10 wt % per trace element chemically dissolved in the biocompatible material; wherein the suture comprises an external polymeric coating.

In another aspect the invention is directed to a method for treating a wound comprising applying the dressings or ointment or cream to the wound, or applying the glue to close the wound.

Other objects and features of the invention are in part apparent and in part pointed out hereinafter.

DESCRIPTION OF PREFERRED EMBODIMENTS

In accordance with this invention, biocompatible and biodegradable glasses containing one or more glass-formers selected from the group consisting of $P_2O_5$, $SiO_2$, and $B_2O_3$ are employed for wound care management. The glasses take various forms, including a flexible three-dimensional compressible body of loose glass-based fibers to be held in place in an open wound, or to be employed as a layer applied over a wound. In another form, the glasses are in the form of particles in an ointment or cream applied to a wound. In yet other forms the glasses are employed as fibers formed into sutures for closing a wound, or as particles in a surgical glue for closing a wound.

Figure 1:
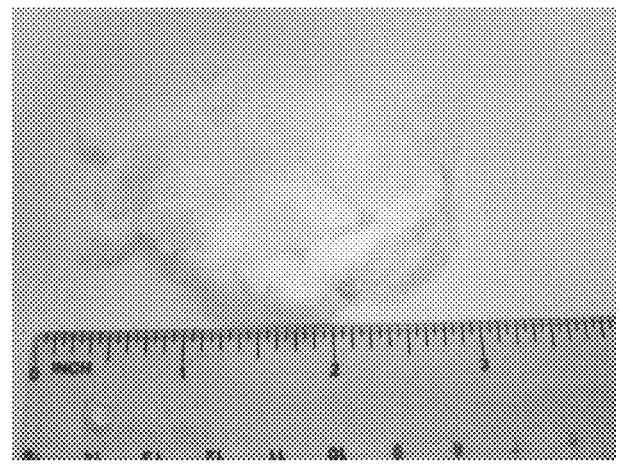
FIG. 1 is a photograph of a three-dimensional compressible body of loose glass-based fibers of the wound care dressing of the invention.
Figure 3:
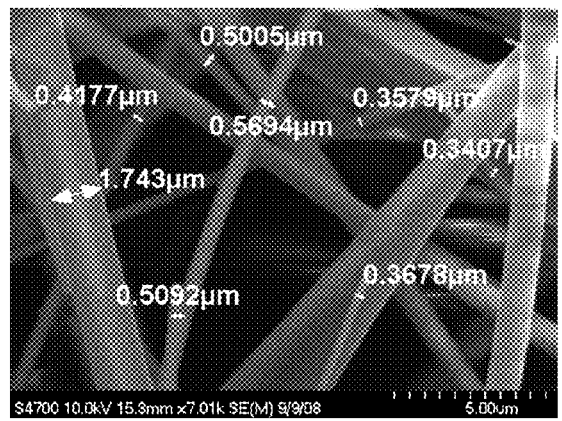
FIG. 3 is a higher magnification SEM image of a body of loose glass-based fibers of the dressing of the invention.

In a first embodiment of the invention which is a three-dimensional compressible body of loose glass-based fibers such as depicted in FIG. 1, the body comprises fibers having a diameter between about 200 nm (0.2 μm (microns)) and about 4000 nm (4 μm). FIG. 3 is an SEM image of such a body showing various fiber diameters at higher magnification. For example, in one embodiment the fibers have a diameter between about 250 nm (0.25 μm) and about 3000 nm (3 μm), such as between about between about 300 nm (0.2 μm) and about 2000 nm (2 μm). The especially small diameter of these fibers renders them highly flexible so they form into the compressible body without breaking. They have a texture like a cotton ball. In certain embodiments the body consists only of fibers meeting these dimensions, while in other embodiments the body includes fibers meeting these dimensional requirements in addition to other glass morphologies, such as fibers of other dimensions, microspheres, particles, ribbons, flakes or the like. The fibers are generally circular in cross section, but they may be flattish or oval or have other-shaped, non-circular cross section, where cross section is the dimension transverse to the fiber's length.

"Diameter" as used herein therefore refers not only to the diameter of a circular cross section, but also to the largest transverse dimension of other, non-circular cross sections.

The number of fibers in the assembly is not narrowly critical to most embodiments, and varies depending on the length of the fibers, size of the dressing, and other factors. For example, in most embodiments, there are hundreds or even thousands of fibers, such as typically at least about 10, at least about 50, or at least about 200 fibers. The upper limit on the number of fibers is dictated by the size of the dressing, and for some embodiments is less than about 50,000, while other embodiments contain more.

Figure 2:
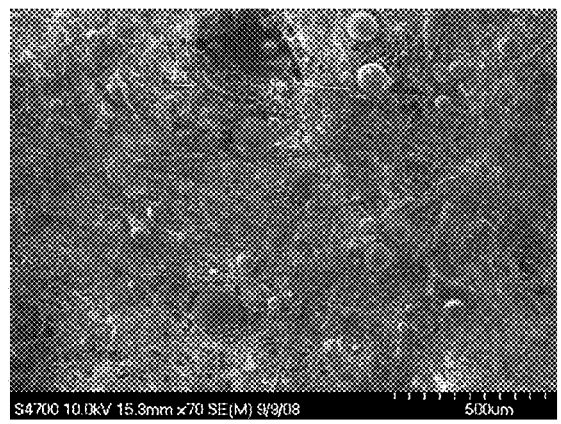
FIG. 2 is a scanning electron microscope (SEM) image of a body of loose glass-based fibers of the invention with glass microspheres interspersed throughout the fibers.

As shown in FIG. 2, the body may also contain, in addition to fine glass fibers, microspheres or beads having a diameter of at least about 10 μm, such as between about 10 μm and about 500 μm, for example between about 20 μm and about 300 μm. In addition to or instead of microspheres, these components may be irregular or regular particles, ribbons, flakes, hollow spheres, or other shapes. While microspheres are preferred in some embodiments, the shape is not narrowly critical in most embodiments, and is to a large extent dictated more by the availability of materials than by other considerations.

The three-dimensional body of glass fibers as a whole has a first state which is unstressed and relaxed when it is in an uncompressed condition such as shown in FIG. 1. The body also has a second state which is stressed when it is in a compressed condition, which generally occurs when the body is shaped and applied to a wound. While the body as a whole is unstressed in its uncompressed condition, the individual fibers are to some extent stressed when they are bent. In the relaxed state, the body has a porosity which is at least about 30% by volume, meaning that at least about 30 vol % of the body is void space not occupied by glass material. For example, in the relaxed state the body is between about 30 vol % and about 90 vol % porosity, such as between about 40 vol % and about 75 vol %. The body may be applied to a wound in an uncompressed state; or it may be compressed so that the porosity is between about 10 vol % and about 75 vol %, such as between about 10 vol % and about 50 vol %. For example, the body may have an uncompressed porosity of between about 40 vol % and 75 vol % and a compressed porosity of between about 10 vol % and about 30 vol %.

The initial surface area of the compressible body varies depending on morphology such as whether it is all fibers, the fiber dimensions, etc. Moreover, the surface area per unit volume changes upon compression, upon application to a wound, and during biodegradation. Generally speaking, a compressible body according to some embodiments of the invention has a surface area/bulk body volume in the relaxed, uncompressed state of the body of between about 1 and about 2000 $cm^{-1}$, such as between about 50 and about 500 $cm^{-1}$.

In the embodiment shown in FIGS. 1 through 3 the fibers are randomly oriented in the body. In alternative embodiments, the fibers may be woven, as may be dictated either by the manner in which the body is formed, or may be dictated by a particular application. For example, in one embodiment the body is in the form of a woven layer which is applied over a wound, similar in morphology to a woven cloth or gauze. The layer may be wrapped around the wound. This layer may constitute the entire dressing, or it may be a component of a multi-component dressing, such as a multilayer dressing. Inasmuch as the layer may constitute the entire dressing, the term "layer" herein is not strictly limited to a layer which is laid over or under another component of the dressing.

When in the form of a layer, the body is also suitable for wrapping around or otherwise applying to an implant such as a hip implant or a bone repair implant. This assists in fixation of the implant in the body. Moreover, the body of glass fibers in this application is suitable for delivering trace elements to the implant site by incorporating trace elements chemically dissolved in the glass material, as described hereinbelow. In these applications where the glass body is a layer, it is flexible. Randomly oriented as well as woven fibers may be employed in these embodiments.

The three-dimensional body has a length, width, and thickness. In irregularly shaped embodiments such as shown in FIG. 1, these dimensions refer to the largest or maximum dimensions in each of the x, y, and z directions. For example, the particular embodiment shown in FIG. 1 has a length of about 75 mm (3 inches as shown by the ruler), a width of about 50 mm, and a thickness of about 5 to 25 mm. Generally speaking, the dimensions of the body are dictated by the size of the wounds for which it is applicable. The body therefore typically has an uncompressed length and width of at least about 10 mm, such as between about 10 mm and about 250 mm, for example between about 10 and about 150 mm, between about 10 and about 50 mm, or between about 50 and 200 mm. The body typically has an uncompressed thickness of at least about 2 mm, such as between about 2 and about 100 mm or between about 5 and 30 mm. The body may be manufactured or supplied to the end users or intermediaries in much larger dimensions, and cut to size by the end users or intermediaries.

In those embodiments where the body is in the form of a layer, the thickness is generally much smaller, for example less than 10 mm, such as between about 1 mm and 10 mm. In one embodiment it is between about 1 and about 3 mm thick. The layer may be in the form of a square, for example having a length and width between about 10 and about 300 mm, or in the form of a rectangle having a width between about 10 and about 75 mm and a length between about 50 and about 250 mm. The layer may also be in the form of a roll having a width between about 10 and about 75 mm and a length greater than 25 mm. In some preferred embodiments where the body is a layer, it has a length and a width which are between about 5 and about 30 times the thickness of the body.

In one embodiment the body is subjected to a bonding operation which at least lightly bonds the fibers and converts the body from a flexible body to a rigid body. This yields a rigid dressing for wound care management comprising a three-dimensional body of bonded glass-based fibers.

The invention in another aspect is a biocompatible ointment or cream for wound care management. This embodiment employs any ointment-based or cream-based carrier which one skilled in the art determines is suitable for treatment of the particular wound. Glass-based particles of a biocompatible material are intermixed in the ointment-based or cream-based carrier. The glass-based particles comprise a glass-former selected from the group consisting of $P_2O_5$, $SiO_2$, $B_2O_3$. The glass-based particles further comprise one or more trace elements selected from the group consisting of Ag, Cu, F, Fe, Mn, Mo, Ni, Sr, and Zn in a concentration between about 0.05 and 10 wt % per trace element chemically dissolved in the biocompatible material.

The invention in another embodiment is a biocompatible surgical glue for closing a wound. The glue comprises an adhesive which one skilled in the art determines is suitable for treatment of the particular wound. The glue also contains particles of a biocompatible material intermixed in the adhesive, wherein the glass-based particles comprise a glass-former selected from the group consisting of $P_2O_5$, $SiO_2$, $B_2O_3$. The particles also contain one or more trace elements selected from the group consisting of Ag, Cu, F, Fe, Mn, Mo, Ni, Sr, and Zn in a concentration between about 0.05 and 10 wt % per trace element chemically dissolved in the biocompatible material. The particle size for glass-based particles in the ointment, cream, or glue is between about 1 and about 300 µm, such as between about 3 and about 50 µm. In the context of the glue, ointment, and cream, the term "particles" includes fibers.

Another embodiment is a surgical suture for closing a wound wherein the suture comprises glass-based fibers of a biocompatible material comprising a glass-former selected from the group consisting of $P_2O_5$, $SiO_2$, $B_2O_3$. The glass-based fibers further comprise one or more trace elements selected from the group consisting of Ag, Cu, F, Fe, Mn, Mo, Ni, Sr, and Zn in a concentration between about 0.05 and 10 wt % per trace element chemically dissolved in the biocompatible material. The suture preferably has an external polymeric coating.

In connection with each of the foregoing embodiments, a trace element such as Ag, Cu, F, Fe, Mn, Mo, Ni, Sr, and Zn, and in some particularly preferred embodiments, Ag, Cu, Sr, Zn, and/or Fe, is preferably incorporated into the glass. Silver has infection-fighting properties. These other elements have an effect on endothelial cell migration which can be useful for blood vessel formation and have importance for tissue regeneration. In this way, these trace elements promote angiogenesis, which is a critical function in promoting tissue growth, such as in wound healing. This is in distinction from promoting osteoconductivity, which refers to providing bone growth factors to a site to promote bone growth. Angiogenesis, which involves increasing vascularity, i.e., vessel growth, is distinct from osteoconductivity.

In those instances when the one or more trace elements are employed, they are incorporated into the glass in a concentration of at least about 0.05 wt %, or at least about 0.1 wt %. In most instances, the concentration is less than 10 wt %, or less than 5 wt %, such as between about 0.05 and about 5 wt %, for example between about 0.1 and about 2.5 wt % (per element). Where the biocompatible glass material is borate-based or phosphate-based, the trace element concentration is less than 5 wt %, and it may be higher and up to 10 wt % where the biocompatible material is silicate-based. The trace elements are selected from the group consisting of Ag, Cu, F, Fe, Mn, Mo, Ni, Sr, and Zn. In certain preferred embodiments the trace element is one or more selected from the group consisting of Ag, Cu, Fe, Sr, and Zn. More than one of these trace elements can be employed in a single composition. Also, certain of these elements may be present in greater amounts in that they are not being used as trace elements in accordance with this invention. For example, a glass which contains 0.4 wt % Cu and 15 wt % Sr contains Cu as a trace element in accordance with this invention; and it contains Sr, but not as a trace element in accordance with this invention. Such a material would indeed satisfy the requirement herein for a trace element from the group Ag, Cu, F, Fe, Mn, Mo, Ni, Sr, and Zn in a concentration between about 0.05 and 10 wt % by virtue of the material's Cu content, regardless of its unqualifying Sr content.

Where Cu is desired, the source of Cu to the glass may be a copper oxide such as CuO or $Cu_2O$ or other copper compounds such as copper nitrate or copper sulfate, for example. In one embodiment, Cu is incorporated in a concentration of between about 0.05 and about 5 wt % (about 0.06-6 wt % CuO; about 0.055-5.5 wt % $Cu_2O$), such as between about 0.1 and about 2.5 wt % (about 0.12-3 wt % CuO; about 0.11-3 wt % $Cu_2O$). There are preferred embodiments employing from about 1 wt % to about 2 wt % Cu, as provided by between about 1.2 wt % and about 2.4 wt % CuO.

Where Sr is desired, the source of Sr to the glass may be an oxide such as SrO or other Sr compounds such as $SrCO_3$, for example. In one embodiment, Sr is incorporated in a concentration of between about 0.05 and about 5 wt % (about 0.06 to 5.90 wt % SrO), such as between about 0.1 and about 2.5 wt % (about 0.12 to 2.95 wt % SrO). There are preferred embodiments employing from about 1 wt % to about 2 wt % Sr, as provided by between about 1.18 wt % and about 2.36 wt % SrO.

Where Zn is desired, the source of Zn to the glass may be an oxide such as ZnO or other Zn compounds such as $Zn_3(PO_4)_2$-$xH_2O$, for example. In one embodiment, Zn is incorporated into the glass in a concentration of between about 0.05 and about 5 wt % (about 0.06 to 6.0 wt % ZnO), such as between about 0.1 and about 2.5 wt % (about 0.12 to 3.0 wt % ZnO). There are preferred embodiments employing from about 1 wt % to about 2 wt % Zn, as provided by between about 1.20 wt % and about 2.40 wt % ZnO.

Where Fe is desired, the source of Fe to the glass may be an oxide such as FeO, $Fe_3O_4$, $Fe_2O_3$, or other Fe compounds such as $FeSO_4$·$7H_2O$, for example. In one embodiment, Fe is incorporated into the glass in a concentration of between about 0.05 and about 5 wt % (about 0.06 to 6.45 wt % FeO), such as between about 0.1 and about 2.5 wt % (about 0.13 to 3.23 wt % FeO). There are preferred embodiments employing from about 1 wt % to about 2 wt % Fe, as provided by between about 1.29 wt % and about 2.58 wt % FeO.

Where Ag is desired, the source of Ag to the glass may be $AgNO_3$ or $AgPO_3$, for example. In one embodiment, Ag is incorporated in a concentration of between about 0.05 and about 5 wt %, such as between about 0.1 and about 2.5 wt %.

The glass formers in certain embodiments of the invention are concentration balanced to impart the desired biodegradability. For example, in one embodiment, the concentrations of the glass formers borate, silicate, and phosphate are balanced to 52.95 wt %, 0 wt %, and 4.0 wt %, respectively, with respect to themselves and with respect to the other components in the material $Na_2O$, CaO, and $K_2O$. Balancing in this regard encompasses balancing the concentration of one glass former with other components, such as with those glasses which contain borate and other components, but no phosphate or silicate.

In many preferred embodiments, the concentrations of glass formers are balanced such that at least about 20 wt % of the glass biodegrades within two weeks of application to a wound. For example, the concentrations of glass formers are balanced such that at least about 20 wt % of the glass biodegrades within two weeks of application to a surface wound of a Fisher 344 rat having an age between 9 and 11 weeks and a weight between 200 and 300 grams. In accord with this measure, the testing is performed on rats with a standard deviation of 25% (relative) of the biocompatible material and a population size of 10. In other words, when 10 of these bodies, ointments, creams, glues, or sutures are applied to rat wounds, on average at least 20 wt % of the glass biodegrades within two weeks; and in at least 68% of rats at least 15 wt % of the glass biodegrades; and in at least 90% of rats at least 10 wt % of the glass degrades. Application for this and the following standards is according to the protocol described below in Example 1. Biodegrading in most instances manifests itself as weight loss, but can also manifest itself as another reaction of the material.

Similarly, in another aspect, the concentrations of glass formers are balanced such that at least about 20 wt % of the trace element concentration in the bodies, ointments, creams, glues, or sutures is released into the host within two weeks of application to its mammalian host. For example, the concentrations of glass formers are balanced such that at least about 20 wt % of the trace element concentration is released into the host within two weeks of application to a Fisher 344 rat having an age between 9 and 11 weeks and a weight between 200 and 300 grams. In accord with this measure, the testing is performed on rats with a standard deviation of 25% (relative) of the biocompatible material and a population size of 10. In other words, when 10 of bodies, ointments, creams, glues, or sutures are applied to rat wounds, on average at least 20 wt % of the trace element concentration is released within two weeks; and in at least 68% of rats at least 15 wt % of the trace element concentration is released; and in at least 90% of rats at least 10 wt % of the trace element concentration is released.

On the other hand, the glass in most embodiments does not biodegrade so quickly upon application to the host that it fails to provide trace elements over a long enough period to adequately promote angiogenesis. For example, at least 30 wt % of the material remains for at least two weeks and does not biodegrade within two weeks. That is, the concentrations of glass formers are balanced such that at least about 30 wt % of the biocompatible glass material remains in the bodies, ointments, creams, glues, or sutures for at least two weeks after application to a Fisher 344 rat having an age between 9 and 11 weeks and a weight between 200 and 300 grams. In accord with this measure, the testing is performed on rats with a standard deviation of 25% (relative) of the glass and a population size of 10. In other words, when 10 of these bodies, ointments, creams, glues, or sutures are applied to rat wounds, on average at least 30 wt % of the glass does not biodegrade within two weeks; and in at least 68% of rats at least 22.5 wt % of the glass does not biodegrade within two weeks; and in at least 90% of rats at least 15 wt % of the glass does not biodegrade within two weeks.

Moreover, in these embodiments, at least 30 wt % of the trace element concentration remains in the bodies, ointments, creams, glues, or sutures for at least two weeks. That is, the concentrations of glass formers are balanced such that at least about 30 wt % of the trace element remains for at least two weeks after application to a Fisher 344 rat having an age between 9 and 11 weeks and a weight between 200 and 300 grams. In accord with this measure, the testing is performed on rats with a standard deviation of 25% (relative) of the biocompatible body material and a population size of 10. In other words, when 10 of these bodies, ointments, creams, glues, or sutures are applied to rat wounds, on average at least 50 wt % of the trace element concentration remains for at least two weeks; and in at least 68% of rats at least 22.5 wt % of the trace element concentration remains in the bodies, ointments, creams, glues, or sutures for at least two weeks; and in at least 90% of rats at least 15 wt % of the trace element concentration remains for at least two weeks.

In one embodiment of the invention the glass releases the trace element at particular rate of release of trace element, per gram of glass, per day in a mammalian host. The release rate can in effect be "dialed in" by determining the desired amount of trace element to be released within the host, and then selecting a biocompatible composition or combination of compositions to achieve this rate. As noted above, the glass formers are concentration balanced to impart the desired biodegradability. In a related aspect, the surface area per unit volume can be controlled to control release rate, as greater surface area increases reactivity and therefore release rate. One skilled in the art appreciates that the rate of biodegradation of the glass is different from host to host, from glass to glass, from trace element to trace element, and otherwise depends on a number of factors. For example, a more physically active host with a faster average heart rate may encourage biodegradation and therefore trace element release at a faster rate. In one embodiment, the composition has a trace element release (Cu) rate of between about 0.5 and about 100 E-7 moles of trace element, per gram of glass, per day; for example, between about 1 and about 25 E-7 moles of trace element, per gram of glass, per day; such as between about 1 and about 20 E-7 moles of trace element, per gram of glass, per day, or between about 3 and about 12 E-7 moles of trace element, per gram of glass, per day.

As noted above, the glass inventive bodies and other forms biodegrades or reacts when in contact with physiological fluids. However, in comparison to articles characterized as "water soluble" which dissolve relatively rapidly (over a period of, e.g., 24 hours or less) in aqueous solutions, the biocompatible materials of the invention are not readily soluble in water or aqueous liquids such as physiological liquids, that is, they slowly react with aqueous liquids over a periods of several days to weeks for the fine fibers and generally weeks to months for the microspheres and larger diameter particles. As understood in the art, materials which are "water soluble" are subject to relatively rapid solubility; and materials which are "water insoluble" are either entirely insoluble in water, or are at least only dissolvable with difficulty. Generally speaking the glass employed in the embodiments of this invention are not water insoluble and are not water soluble under this characterization; rather, they are of intermediate water solubility.

The glass material of the bodies, ointments, creams, glues, or sutures is biocompatible in that it is not toxic or otherwise harmful to its host's living tissue. Some of the preferred compositions (Ca-free) of the invention are also not bioactive, in the sense that hydroxyapatite does not form. That is, they lack bioactivity, where bioactivity refers to a material's capacity in phosphorus-containing mammalian fluids to foster growth of a calcium phosphate layer or convert to bone-precursor calcium phosphate compounds which, in turn, promotes bone bonding to the material.

In one embodiment the glass employed is a borate-based glass material containing the following, approximately, with all percentages herein being by weight, unless stated otherwise:

| | |
|---|---|
| $B_2O_3$ | 40 to 80 |
| $Na_2O$ | 0 to 25 |
| $Li_2O$ | 0 to 25 |
| $K_2O$ | 0 to 25 |
| $Rb_2O$ | 0 to 25 |
| CaO | 0 to 40 |
| MgO | 0 to 25 |
| SrO | 0 to 40 |
| BaO | 0 to 50 |
| $Li_2O + Na_2O + K_2O + Rb_2O$ | 0 to 50 cumulative |
| MgO + SrO + BaO + CaO | 0 to 50 cumulative |
| $P_2O_5$ | 0 to 10 |
| $SiO_2$ | 0 to 18 |
| $Al_2O_3$ | 0 to 3 |
| F | 0 to 4 |
| transition metal elements | 0 to 10 cumulative. |

The concentrations of $K_2O$ and MgO in certain of these embodiments are each from about 1 to about 25 wt %. In most embodiments, the one or more of $Li_2O$, $Na_2O$, $K_2O$, and $Rb_2O$ is present in a cumulative concentration between about 1 and about 50 wt %, such as between about 5 and about 20 wt %; and the one or more of MgO, SrO, BaO, and CaO is present in a cumulative concentration between about 1 and about 50 wt %, such as between about 5 and about 40 wt %. Where Cu is an optionally included trace element, this composition further contains 0.05 to 5; or 0.01 to 2.5 wt % Cu; as CuO, $Cu_2O$, or other Cu compound. The transition metal elements are those elements where the d-band contains less than its maximum number of ten electrons per atom, and includes, among others, Co and Ni. In fact, certain of the trace elements used in accordance with this invention such as Zn and Fe are transition metals. So in formulations where the trace element concentration of these trace elements is stated to be in a particular range such as between about 0.1 and about 2.5 wt %, of course the trace element concentration is in that range regardless of the fact that transition elements may be among the trace elements, and if Zn and Fe are present in an amount greater than 2.5 wt %, they are not trace elements.

A few exemplary glass materials useful in the invention are as follows:

TABLE 1

Trace-Element-Containing Borate Biocompatible Glasses (wt %)

| Glass | $B_2O_3$ | $Na_2O$ | CaO | $K_2O$ | MgO | $P_2O_5$ | CuO | SrO | ZnO | $Fe_2O_3$ |
|---|---|---|---|---|---|---|---|---|---|---|
| 1 | 52.95 | 5.99 | 19.98 | 11.99 | 5.00 | 4.00 | 0.10 | | | |
| 2 | 52.89 | 5.99 | 19.96 | 11.98 | 4.99 | 3.99 | 0.20 | | | |
| 3 | 52.79 | 5.98 | 19.92 | 11.95 | 4.98 | 3.98 | 0.40 | | | |
| 4 | 52.47 | 5.94 | 19.80 | 11.88 | 4.95 | 3.96 | 1.00 | | | |
| 5 | 51.94 | 5.88 | 19.60 | 11.76 | 4.90 | 3.92 | 2.00 | | | |
| 6 | 51.73 | 5.86 | 19.52 | 11.71 | 4.88 | 3.90 | 0.40 | 2.00 | | |
| 7 | 51.20 | 5.80 | 19.32 | 11.59 | 4.83 | 3.86 | 0.40 | 2.00 | 1.00 | |
| 8 | 50.88 | 5.76 | 19.20 | 11.52 | 4.80 | 3.84 | 0.40 | 2.00 | 1.00 | 0.40 |

In most embodiments the compressible body or glass particles consist only or essentially of components meeting these compositional requirements or other narrower descriptions herein. But generally speaking, for some embodiments other materials not meeting these descriptions may be incorporated.

Additional borate-based materials within this description, into which Ag, Cu or other stated trace element may be incorporated according to this invention, contain, by weight %, the following, keeping in mind that one or more of the other trace elements may be included in addition to Cu in analogous concentrations, or instead of Cu.

TABLE 2

Wt. % Composition of Additional Borate Glasses

|   | $B_2O_3$ | $Na_2O$ | $K_2O$ | $Li_2O$ | CaO | BaO | MgO | $P_2O_5$ | CuO |
|---|---|---|---|---|---|---|---|---|---|
| A | 52.5 | 6.0 | 12.0 |  | 20.0 |  | 5.0 | 4.0 | 0.5 |
| B | 70.3 |  |  | 10.3 | 19.3 |  |  |  | 0.1 |
| C | 63.7 | 19.0 |  |  | 17.2 |  |  |  | 0.1 |
| D | 49.0 | 14.6 |  |  |  | 36.0 |  |  | 0.4 |
| E | 78.4 |  |  | 11.5 | 10.0 |  |  |  | 0.1 |
| F | 69.9 |  |  | 10.0 | 10.0 | 10.0 |  |  | 0.1 |
| G | 78.6 |  |  | 11.3 |  |  | 10.0 |  | 0.1 |
| H | 78.6 |  |  | 11.3 | 10.0 |  |  |  | 0.1 |
| I | 75.9 |  |  | 11.0 | 13.0 |  |  |  | 0.1 |
| J | 58.6 |  |  | 8.0 | 33.0 |  |  |  | 0.4 |

It can therefore be appreciated that in addition to the Cu, and/or in addition to Ag, Cu, F, Fe, Mn, Mo, Sr, and/or Zn, the borate-based biocompatible glass materials include 40 to 80 wt % $B_2O_3$ or 50 to 80 wt % $B_2O_3$, or even the narrower $B_2O_3$ ranges described herein, in combination with 1 to 25 wt % $Na_2O$, 1 to 25% $K_2O$, 1 to 40 wt % CaO, 1 to 25 wt % MgO, and 1 to 10 wt % $P_2O_5$. Or the component materials may contain 40 to 80 wt % $B_2O_3$, 1 to 25 wt % $Li_2O$, and 1 to 40 wt % CaO. Or they may contain 40 to 80 wt % $B_2O_3$, 1 to 25 wt % $Na_2O$, and 1 to 40 wt % CaO. Or they may contain 40 to 80 wt % $B_2O_3$, 1 to 25 wt % $Na_2O$, and 1 to 40 wt % BaO. Or they may contain 40 to 80 wt % $B_2O_3$, 1 to 25 wt % $Li_2O$, and 1 to 25 wt % MgO. Or they may contain 40 to 80 wt % $B_2O_3$, 1 to 25 wt % $Li_2O$, and 1 to 40 wt % BaO. While the biocompatible materials hereinabove and hereinbelow are described as containing various oxides by weight %, those skilled in the art understand that in the final glass or glass/crystalline composition, the oxide compounds are dissociated, and the specific oxides, e.g., $B_2O_3$, $SiO_2$, $P_2O_5$, etc. are not separately identifiable or even necessarily separately present. Nonetheless, it is conventional in the art to refer to the final composition as containing a given % of the individual oxides, so that is done here. So from this perspective, the compositions herein are on an equivalent basis.

The biocompatible glass employed in the invention containing the trace element in certain preferred versions are borate-based in that they contain between about 40 and about 80 wt % $B_2O_3$, such as between about 50 and about 80 wt % $B_2O_3$. Borate-based materials have several important advantages for biological use such as their ease of preparation, ability to be made into glass particulates, microspheres or fibers at relatively low temperatures without crystallization, and, particularly, their biocompatibility. The borate-based materials disclosed herein, compared to silicate-based materials, have significantly faster reaction rates, lower melting temperatures, resistance to crystallization, and in certain instances the absence of silica, which only slowly degrades in the body. So while certain embodiments employ up to about 18 wt % $SiO_2$ in many other preferred embodiments herein, the materials are silicate-free, containing less than 0.1 wt % silicate or even no silicate. Borate glass fibers often form hollow fibers upon reaction in-vivo, while silicate glasses do not; and they facilitate angiogenesis in-vivo. The borate materials described herein also release boron in-vivo as they react with the body fluids.

There is one embodiment which has specific preference in certain applications and wherein the concentration of Ca (elemental or in CaO or other compounds) in the glass is controlled to less than about 5 wt %. Certain preferred embodiments strictly control the Ca concentration to less than about 0.5 wt %, such as to less than 0.2 wt %, and even to less than 0.1 wt %. The advantage in this embodiment to strictly controlling Ca concentration is the avoidance of the formation of calcium phosphate compounds, apatite type compounds, and related amorphous calcium phosphate (ACP) upon exposure to physiological phosphorus-containing fluids. Such apatite compounds include hydroxyapatite $Ca_5(PO_4)_3(OH)$, fluoroapatite $Ca_5(PO_4)_3F$, amorphous calcium phosphate (ACP), and other calcium-containing compounds. Thus, in certain applications it is advantageous to avoid the formation of Ca-apatite compounds because they have a relatively lower radiopacity than do, for example, analogous Sr or Ba compounds. In certain situations it is advantageous to avoid Ca-apatite compounds in order to form compounds which degrade more rapidly, or perhaps even more slowly. It can also be advantageous to avoid Ca for purposes of controlling melt characteristics, such as viscosity, melting temperature, and/or crystallization tendency. The Ca-free compositions lack bioactivity, where bioactivity refers to a material's capacity in phosphorus-containing mammalian fluids to foster growth of a calcium phosphate layer or convert to bone-precursor calcium phosphate compounds.

The biocompatible Ca-free material employed for certain embodiments preferably contains between about 40 and about 90 wt % $B_2O_3$ with the remainder being selected from alkali oxides and alkaline earth oxides, and other optional constituents listed below. For example, this material contains, by weight %:

| | |
|---|---|
| $B_2O_3$ | 40 to 80 |
| $Na_2O$ | 0 to 25 |
| $Li_2O$ | 0 to 25 |
| $K_2O$ | 0 to 25 |
| $Rb_2O$ | 0 to 25 |
| MgO | 0 to 25 |
| SrO | 0 to 40 |
| BaO | 0 to 25 |
| $Li_2O$ + $Na_2O$ + $K_2O$ + $Rb_2O$ | 0 to 50 cumulative |
| MgO + SrO + BaO | 0 to 50 cumulative |
| $P_2O_5$ | 0 to 10 |
| $SiO_2$ | 0 to 18 |
| $Al_2O_3$ | 0 to 3 |
| F | 0 to 4 |
| transition metal elements | 0 to 10 cumulative. |

In addition, the material optionally contains Cu in a concentration of 0.05 to 5; or 0.01 to 2.5 wt %, as CuO, $Cu_2O$, or other Cu compound, and/or other trace element. Certain of these embodiments contain low levels of Ca, as described above; while others are substantially Ca-free and contain essentially no or less than 0.1 wt % Ca.

In one preferred embodiment, the glass contains between about 50 and about 80 wt % $B_2O_3$; between about 5 and about 20 wt % alkali oxide component selected from the group consisting of $Li_2O$, $Na_2O$, $K_2O$, $Rb_2O$, and combinations thereof; and between about 5 and about 40% alkaline earth component selected from the group consisting of MgO, SrO, BaO, and combinations thereof. Optional components include $P_2O_5$, $SiO_2$, $Al_2O_3$, F, and transition metal elements. Lanthanides are specifically and strictly excluded from certain preferred embodiments. In some embodiments the biocompatible material consists essentially of between about 50 and about 80 wt % $B_2O_3$; between about 5 and about 20 wt % alkali oxide component selected from the group consisting of $Li_2O$, $Na_2O$, $K_2O$, $Rb_2O$, and combinations thereof; between about 5 and about 40 wt % alkaline earth component selected from the group consisting of MgO, SrO, BaO, and combinations thereof, and between about 0.05 and 5 wt % Cu, as CuO, $Cu_2O$, or other Cu compound Exemplary borate-based Ca-free materials, into which Cu may be incorporated according to this invention, contain, by weight %, the following; keeping in mind that one or more of the other trace elements may be included in addition to Cu in analogous concentrations, or instead of Cu:

TABLE 3

Wt. % Composition of Ca-Free Borate Glasses

| | $B_2O_3$ | $Na_2O$ | $Li_2O$ | MgO | BaO | CuO |
|---|---|---|---|---|---|---|
| I | 49.0 | 14.6 | | | 36.1 | 0.3 |
| II | 78.7 | | 11.1 | 10.0 | | 0.2 |
| III | 78.7 | | 11.1 | | 10.0 | 0.2 |
| IV | 75.8 | | 11.0 | | 13.0 | 0.2 |
| V | 58.7 | | 8.0 | | 33.0 | 0.3 |
| VI | 45.0 | | 6.6 | | 48.0 | 0.4 |
| VII | 69.7 | | 10.0 | 10.0 | 10.0 | 0.3 |

In certain embodiments of the invention, the glass is selected to include at least two of the alkali oxides $Li_2O$, $Na_2O$, $K_2O$, and/or $Rb_2O$ in a cumulative concentration of between about 5 and about 25 wt %, such as between about 8 and 20 wt %. It has been discovered to be advantageous to include two or more such alkali compounds in order to reduce the tendency for crystallization, which ultimately improves the workability and manufacturability of the glasses. Using more than one type of alkali (i.e., mixed alkali) can reduce the cost of a glass, modify its reaction rate with body fluids, and provide additional elements beneficial to tissue growth and regeneration.

A further feature of certain embodiments is that the cumulative concentration of the alkaline earth oxides from the group consisting of MgO, SrO, BaO, CaO, and combinations thereof is in the range of 1 to about 50 wt %, such as in the range of 1 to 30 wt %, or even about 8 to 25 wt %. Certain of these embodiments contain two or more such alkaline earth oxides in a range of 1 to 45 wt % cumulatively, such as in the range of 5 to 25 wt %. If SrO is present in a concentration which yields a Sr concentration above 10 wt %, it does not qualify as a trace element in accordance with this description.

These embodiments into which Cu and/or other trace element may be incorporated and which employ mixed alkali oxide contents contain $B_2O_3$ from about 40 to about 80 wt %. Certain of these embodiments consist essentially of $B_2O_3$ from about 40 to about 80 wt %, mixed alkali oxides selected from the group consisting of $Li_2O$, $Na_2O$, $K_2O$, and $Rb_2O$, and one of MgO, SrO, BaO, or CaO, plus the Cu or other trace element compound. Other embodiments consist essentially of $B_2O_3$ from about 40 to about 80 wt %, two or more alkali oxides selected from the group consisting of $Li_2O$, $Na_2O$, $K_2O$, and $Rb_2O$, and two or more alkaline earth oxides from the group consisting of MgO, SrO, BaO, and CaO, plus the Cu or other trace element compound. For example, composition A in Table 2 consists essentially of $B_2O_3$ from about 40 to about 80 wt %, two or more mixed alkali oxides selected from the group consisting of $Li_2O$, $Na_2O$, $K_2O$, and $Rb_2O$ in a cumulative wt % between 5 and 25%, and two or more from among MgO, SrO, BaO, and CaO in a cumulative wt % between 8 and 25%. Other embodiments optionally include one or more of $P_2O_5$, $SiO_2$, $Al_2O_3$, F, and transition metal elements.

The invention includes using fibers or particles from biocompatible glass materials with an especially high $B_2O_3$ composition, namely, from about 60 to about 82 wt %, preferably from about 70 to about 80 wt %. These embodiments employ an alkali oxide selected from the group consisting of $Li_2O$, $Na_2O$, $K_2O$, $Rb_2O$, and combinations thereof cumulatively from about 1 to about 50 wt %, such as from about 5 to about 25 wt %, and even from about 8 to about 20 wt %; and even optionally two or more such oxides cumulatively in this range. They also optionally employ alkaline earth oxides from group consisting of MgO, SrO, BaO, CaO, and combinations thereof in the range of about 1 to about 50 wt %, such as in the range of 1 to 30 wt %, or even about 8 to 25 wt %, and even two or more such oxides cumulatively in this range. Certain of these embodiments consist essentially of these components, such as compositions II, III, IV, and VII in Table 3; while other embodiments optionally include one or more of $P_2O_5$, $SiO_2$, $Al_2O_3$, F, and transition metal elements.

In the foregoing described mixed-alkali and high-borate embodiments, the Ca concentration may be strictly controlled to less than about 5 wt %, including to less than 0.5 wt %, such as to less than 0.2 wt % or less than 0.1 wt % to avoid the formation of Ca compounds, in the manner discussed above. Alternatively, there are embodiments containing two or more alkali oxides which also contain CaO in an amount up to about 40 wt % to facilitate the formation of hydroxyapatite, other calcium phosphate compounds, or amorphous calcium phosphate.

Some exemplary materials of the invention contain, approximately, 40 to 80 wt % $B_2O_3$, 0.05 to 5% CuO, and $Na_2O$, $K_2O$, MgO, and $P_2O_5$. More specific examples contain or even consist essentially of 40 to 90 wt % $B_2O_3$, 0.1 to 5% CuO, 1 to 25 wt % $Na_2O$, 1 to 25 wt % $K_2O$, 1 to 25 wt % MgO, and 1 to 10 wt % $P_2O_5$.

The invention in other embodiments employs glasses formed from a phosphate-based or silicate-based material which is at least partially dissolvable in mammalian bodily fluids, and Cu or other trace element is optionally incorporated into the biocompatible material in a concentration as described above. In these embodiments, $P_2O_5$ and/or $SiO_2$ are glass formers and constitute about 20 to about 65 wt % $P_2O_5$ or about 20 to about 60 wt % $SiO_2$. These materials also contain an alkali metal oxide component of, for example, one or more of $Li_2O$, $Na_2O$, $K_2O$, $Rb_2O$, $Cs_2O$, or a mixture thereof in a concentration of about 8 wt % to about 55 wt %, such as about 10 to about 52 wt %. Many of these phosphate- and silicate-based glasses also contain a calcium component, one of CaO, $CaF_2$, or mixtures thereof. For example, many of these glasses contain from about 5 to about 40 wt % of CaO or $CaF_2$, or mixtures thereof, such as about 10 to about 30 wt % of CaO or CaF$_2$, or mixtures thereof, or about 10 to about 15 wt % of CaO or CaF$_2$, or mixtures thereof. Accordingly, one of these embodiments contains about 20 to about 65 wt % P$_2$O$_5$, and one or more of Li$_2$O, Na$_2$O, K$_2$O, Rb$_2$O, Cs$_2$O, or a mixture thereof in a concentration of about 8 wt % to about 55 wt %, and a calcium component in a concentration of about 5 to about 40 wt % of CaO or CaF$_2$, and optionally Cu in a concentration of about 0.05 to about 5 wt %, such as between about 0.1 and about 2.5%. Another embodiment contains about 20 to about 65 wt % P$_2$O$_5$, and one or more of Li$_2$O, Na$_2$O, K$_2$O, Rb$_2$O, Cs$_2$O, or a mixture thereof in a concentration of about 10 wt % to about 52 wt %, a calcium component of CaO or CaF$_2$ or mixtures thereof in a concentration of about 5 wt % to about 40 wt % of CaO or CaF$_2$ or mixtures thereof, and Cu or other trace element in a concentration of about 0.05 to about 5 wt %, such as between about 0.1 and about 2.5%. Another embodiment contains about 20 to about 65 wt % P$_2$O$_5$, and one or more of Li$_2$O, Na$_2$O, K$_2$O, Rb$_2$O, Cs$_2$O, or a mixture thereof in a concentration of about 8 wt % to about 55 wt %, a calcium component of CaO or CaF$_2$ or mixtures thereof in a concentration of about 10 to about 30 wt % of CaO or CaF$_2$ or mixtures thereof, and Cu or other trace element in a concentration of about 0.05 to about 5 wt %, such as between about 0.1 and about 2.5%. Another of these embodiments contains about 20 to about 60 wt % SiO$_2$, and one or more of Li$_2$O, Na$_2$O, K$_2$O, Rb$_2$O, Cs$_2$O, or a mixture thereof in a concentration of about 8 wt % to about 55 wt %, a calcium component of CaO in a concentration of about 5 to about 40 wt % of CaO or CaF$_2$, and Cu or other trace element in a concentration of about 0.05 to about 5 wt %, such as between about 0.1 and about 2.5 wt %. Another embodiment contains about 20 to about 60 wt % SiO$_2$, and one or more of Li$_2$O, Na$_2$O, K$_2$O, Rb$_2$O, Cs$_2$O, or a mixture thereof in a concentration of about 10 wt % to about 52 wt %, a calcium component of CaO or CaF$_2$ or mixtures thereof in a concentration of about 5 wt % to about 40 wt % of CaO or CaF$_2$ or mixtures thereof, and optionally Cu or other trace element in a concentration of about 0.05 to about 5 wt %, such as between about 0.1 and about 2.5 wt %. Another embodiment contains about 20 to about 60 wt % SiO$_2$, and one or more of Li$_2$O, Na$_2$O, K$_2$O, Rb$_2$O, Cs$_2$O, or a mixture thereof in a concentration of about 8 wt % to about 55 wt %, a calcium component of CaO or CaF$_2$ or mixtures thereof in a concentration of about 10 to about 30 wt % of CaO or CaF$_2$ or mixtures thereof, and optionally Cu or other trace element in a concentration of about 0.05 to about 5 wt %, such as between about 0.1 and about 2.5 wt %. In certain of these embodiments, CaF$_2$ is strictly avoided and the calcium component is CaO.

Examples of silicate-based glasses containing Cu and other trace elements useful in this invention are as follows:

Examples of phosphate-based biocompatible glass containing Cu or other trace element and useful in this invention are shown in Table 5.

TABLE 5

Weight Percent Composition of Phosphate-Based Biocompatible Glasses

| Glass ID | Na$_2$O | K$_2$O | CaO | MgO | B$_2$O$_3$ | P$_2$O$_5$ | Li$_2$O | SrO | CuO |
|---|---|---|---|---|---|---|---|---|---|
| P-1 | 3.8 | 5.8 | 27.5 | 2.5 | 0.0 | 60.0 | 0.0 | 0.0 | 0.4 |
| P-2 | 9.2 | 9.3 | 27.5 | 0.0 | 0.0 | 53.5 | 0.0 | 0.0 | 0.5 |
| P-3 | 7.8 | 11.8 | 17.0 | 7.6 | 0.0 | 55.2 | 0.0 | 0.0 | 0.6 |
| P-4 | 7.8 | 11.8 | 17.0 | 7.6 | 0.0 | 55.2 | 0.0 | 0.0 | 0.6 |
| P-5 | 6.6 | 8.9 | 21.9 | 0.0 | 4.1 | 58.0 | 0.0 | 0.0 | 0.5 |
| P-6 | 10.5 | 0.0 | 23.0 | 0.0 | 4.0 | 61.1 | 1.1 | 0.0 | 0.3 |
| P-7 | 8.0 | 3.7 | 1.5 | 0.0 | 1.8 | 78.1 | 0.0 | 6.7 | 0.2 |

These phosphate-based formulations demonstrate situations where it is advantageous to include at least two of the alkali oxides Li$_2$O, Na$_2$O, K$_2$O, and/or Rb$_2$O in a cumulative concentration of between about 5 and about 25 wt %, such as between about 8 and 20 wt %. As noted above, it has been discovered to be advantageous to include two or more such alkali compounds in order to reduce the tendency for crystallization, which ultimately improves the workability and manufacturability of the glasses, which can be important to making fibers. Using more than one type of alkali (i.e., mixed alkali) can reduce the cost of a glass, modify its reaction rate with body fluids, and provide additional elements beneficial to tissue growth and regeneration.

A further feature of these phosphate-based embodiments is that the cumulative concentration of the alkaline earth oxides from the group consisting of MgO, SrO, BaO, CaO, and combinations thereof is in the range of 1 to about 50 wt %, such as in the range of 1 to 30 wt %, or even about 8 to 25 wt %. Certain of these embodiments contain two or more such alkaline earth oxides in a range of 1 to 45 wt % cumulatively, such as in the range of 5 to 25 wt %.

There is also an option with this invention of employing distinct component compositions to strategically impart certain properties. For example, the compressible body, ointment, cream, glue, or suture in some embodiments employs 10 to 90 wt % of components having one composition selected from the above, and 10 to 90 wt % of components of a different composition. Or even more than two such types of components may be employed. That is, the material may contain at least 10 wt % of components comprising a first component material within the contemplated compositions and at least 10 wt % of components comprising a second component material, wherein the first and second component materials have compositions distinct from each other. And it is contemplated that only the first component

TABLE 4

Weight Percent Composition of Silicate-Based Biocompatible Glasses (wt %)

| Glass | SiO$_2$ | Na$_2$O | P$_2$O$_5$ | CaO | CuO | FeO | CaF$_2$ | B$_2$O$_3$ | ZnO | MnO | MgO | K$_2$O |
|---|---|---|---|---|---|---|---|---|---|---|---|---|
| A | 44.6 | 24.3 | 5.9 | 24.3 | 1.0 | | | | | | | |
| B | 44.1 | 24.0 | 5.9 | 24.0 | 2.0 | | | | | | | |
| C | 43.7 | 23.8 | 5.8 | 23.8 | 3.0 | | | | | | | |
| D | 43.2 | 23.5 | 5.8 | 23.5 | 4.0 | | | | | | | |
| E | 42.8 | 23.3 | 5.7 | 23.3 | 5.0 | | | | | | | |
| F | 44.0 | 25.0 | 6.0 | 20.0 | 0.2 | 0.2 | 1.0 | 2.2 | 0.6 | 0.2 | 0.6 | |
| G | 50.0 | 6.0 | | 19.0 | 0.2 | 0.2 | 1.0 | 3.0 | 1.0 | 0.2 | | 12.0 | material may contain Cu and/or other trace element. This permits the selection of, for example, faster reacting fibers or particles in combination with slower reacting fibers or particles; or the selection of Ca-containing fibers or particles with Ca-free fibers or particles. One can therefore select standard composition components and combine them with non-standard composition components to effectively customize or dope the overall composition for the application presented, or for the host's particular needs. Alternatively, hollow spheres containing a growth factor or drug for delivery to the host can be incorporated with the compressible body, ointment, cream, glue, or suture.

The method of making the glass is not narrowly critical to the invention. By way of example, in preparing the glass, individual analytical reagent grade components are weighed, mixed thoroughly, and melted in a platinum crucible at temperatures ranging from 900 to 1500° C. for approximately one to four hours. The melt is then quenched, for example, on a steel or copper plate to form glass that can be ground into particulates of a desired size. The material of preferred compositions when in the form of a melt can easily be formed into fibers or particles. Fibers can either be pulled by hand directly from the melt or pulled through bushing by a rotating drum.

The biocompatible material may be glassy, glass ceramic, or ceramic in nature. However the glassy state is preferred in this invention because, generally speaking, glassy materials are stronger and more chemically homogeneous than their crystalline or partially crystalline counterparts of the same composition. In this description, the term "glass" is used to include materials which are entirely glassy as well as materials which are part glassy and part crystalline. It is therefore preferable that the biocompatible material is substantially glass in that less than about 5 wt %, more preferable less than 1 wt %, of the component material is crystalline material. The glass used in many embodiments of the invention, consistent with the foregoing description, are at least 99 wt % an amorphous or non-crystalline solid, for example made by fusing a mixture of oxides such as one or more of $SiO_2$, $B_2O_3$, $P_2O_5$ (known as glass forming oxides) with basic oxides such as the alkali and alkaline earth oxides, along with the optional one or more trace element compounds such as Cu compounds. In an alternative embodiment, the fibers or particles include glass ceramics fibers that contain both glassy and crystalline regions which in many respects function in the same manner as a fiber that is completely (100%) non-crystalline. The fibers or particles may alternatively be pre-reacted biocompatible glasses such as glass fibers or particles pre-reacted to have a thin surface layer of hydroxyapatite.

Example 1

The dressing comprising a compressible body of loose glass-based fibers of FIG. 1 was prepared from glass of composition 53 wt % $B_2O_3$, 20 wt % CaO, 12 wt % $K_2O$, 6 wt % $Na_2O$, 5 wt % MgO, 4 wt % $P_2O_5$. As shown in FIG. 2, there were some residual beads (microspheres) of that are formed as part of the process for forming fibers. The diameter of the fibers ranged from of about 300 nm to about 2000 nm, as shown in FIG. 3. The microspheres were much larger in diameter and ranged from approximately 20 microns to about 300 microns as shown in FIG. 2.

Figure 4:
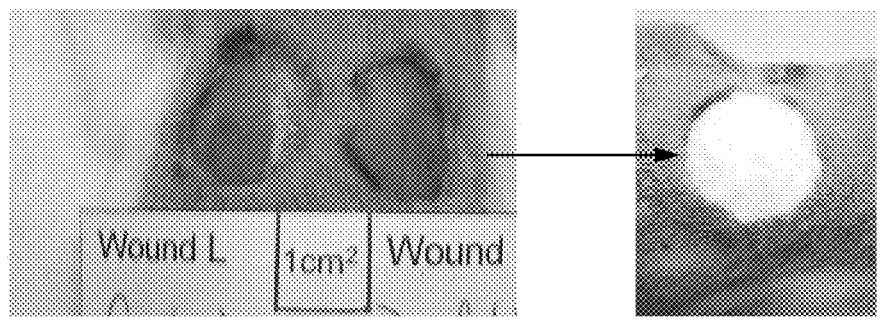
FIGS. 4 through 14 are photographs showing the healing progression of wounds as described hereinbelow.
Figure 5:
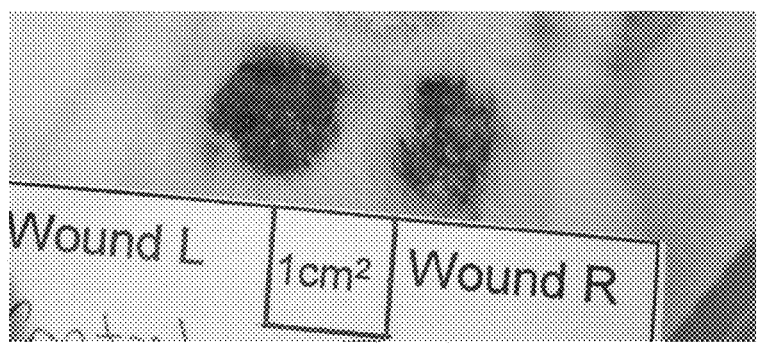
Figure 6:
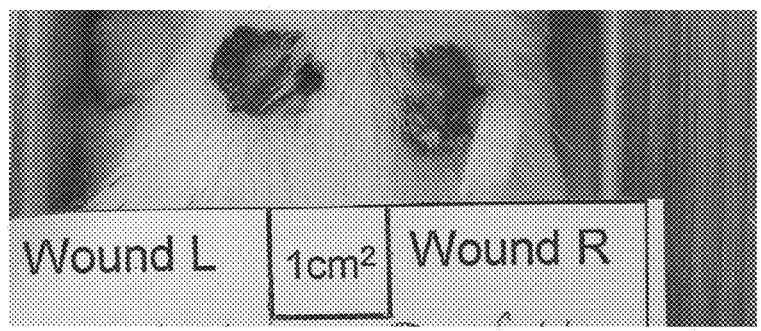
Figure 7:
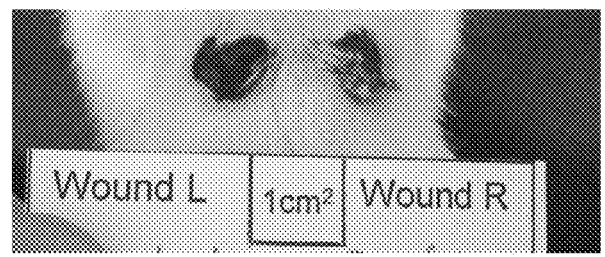
Figure 8:
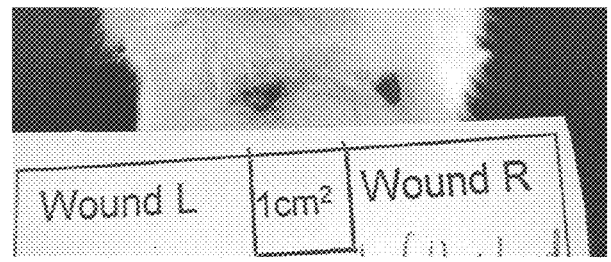
Figure 9:
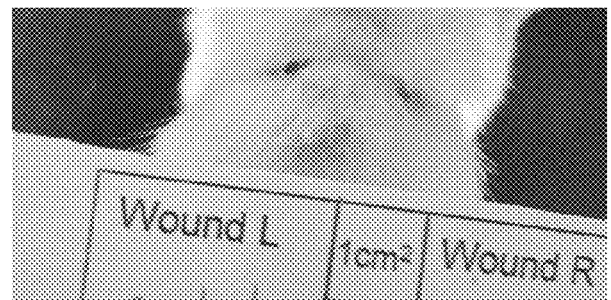
Figure 10:
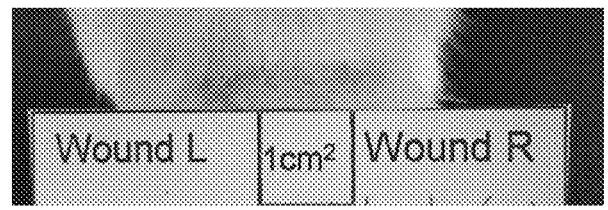

The compressible body of FIG. 1 was used in an experiment to fill a cutaneous defect in a rat. It was shaped by hand to form a disk about 15 mm in diameter and about 2 mm thick. This cylinder was placed in a wound as shown in FIG. 4. The rats were Fisher 344 rats having an age between 9 and 11 weeks and a weight between 200 and 300 grams. Prior to implantation, the dressings were washed twice with ethyl alcohol and heat sterilized at 250° C. for 2.5 hours in a small box furnace. For application, the back of the rat was shaved, sterilized with iodine, and washed with 70% ethanol. Each rat was anesthesized with a mixture of isofluorine and medical grade oxygen. After application of the dressing, 0.1 mL of Penicillin G Procaine was injected into each thigh of the rat to prevent infection. The rats were placed on a heating pad in a cage with fresh air during recovery.

FIGS. 5 through 10 show a representative set of images showing the healing progression of a control wound (left side) and a wound covered with the compressible body (right side). The day 0 image clearly shows the wound covered with the dressing (white area) that fills the entire wound. The two wounds were monitored for about three weeks as shown by the images of FIGS. 5 through 10, which show that the wound covered by the dressing healed at approximately the same rate as the control wound.

Figure 11:
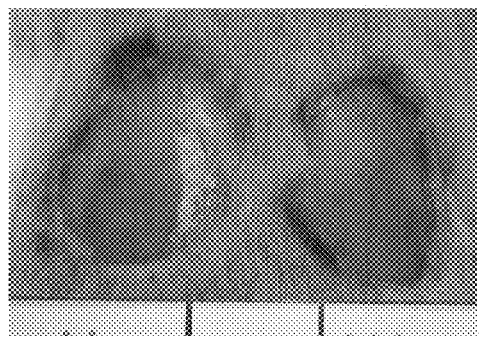
Figure 12:
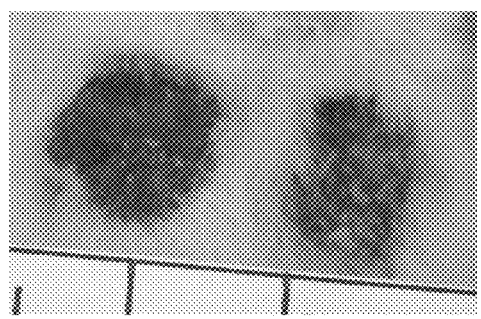
Figure 13:
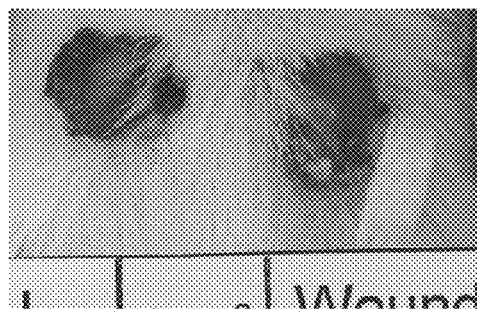
Figure 14:

FIGS. 11 through 14 show a few selected higher magnification images to illustrate the benefits of the dressing. The control (no dressing) is on the left and the wound covered with the fiber dressing is on the right. FIG. 11 shows the open wounds on day 0. The wounds are moist and the exposed tissue appears healthy. FIG. 12 shows the wounds after four days, revealing that the tissue of the control wound was dried and dark grey in appearance while the side covered with the dressing looks like a normal scab. The scab generated by the dressing reacting with the underlying tissue appears to have formed a beneficial temporary barrier. In FIGS. 13 and 14, the scab can be seen peeling away from the wound as the wound closes. The scab on the control side in FIGS. 13 and 14 is still dark in color and dry.

Figure 15:
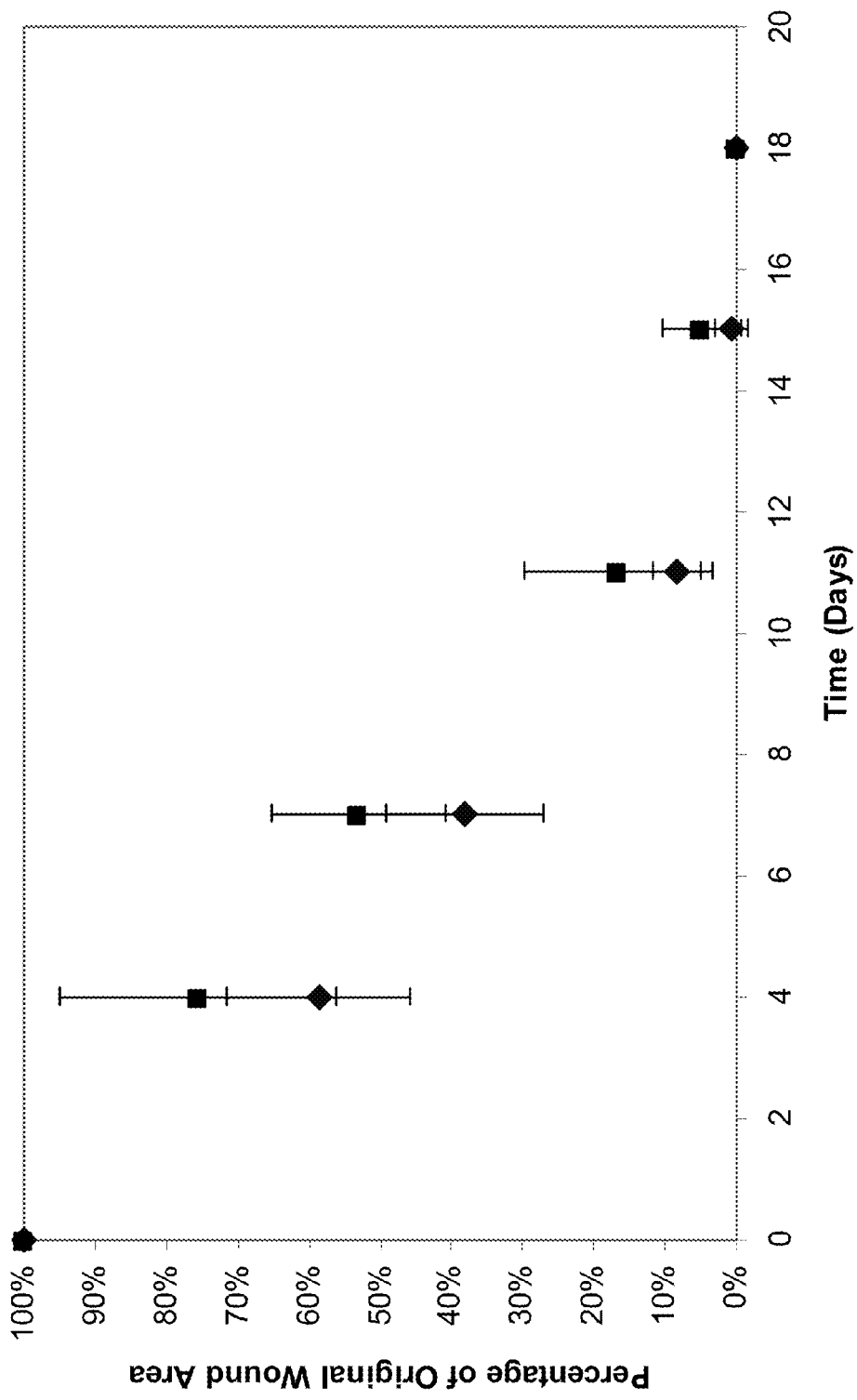
FIG. 15 is a graphical depiction of wound area as a function of time as described hereinbelow.

The area of each wound was measured periodically, and the average area for each control and wound covered with dressing was calculated and plotted vs. time. The graph in FIG. 15 shows there was little difference between the closure of the control wound and the dressing-covered wound. However, the dressing-covered wound had a barrier protecting it from its surroundings, and while possibly slowing the wound closure initially, the barrier likely helped keep out harmful pathogens.

Figure 16:
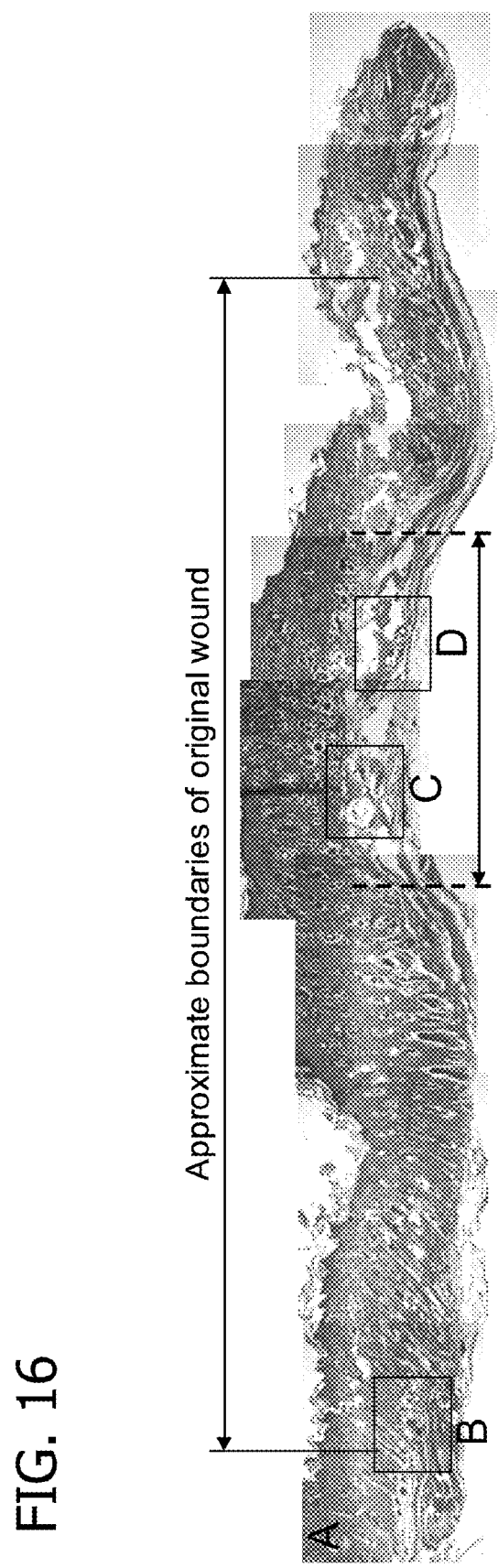
FIGS. 16 through 20 are photographs of histological staining (H&E) of a wound treated according to this invention.
Figure 18:
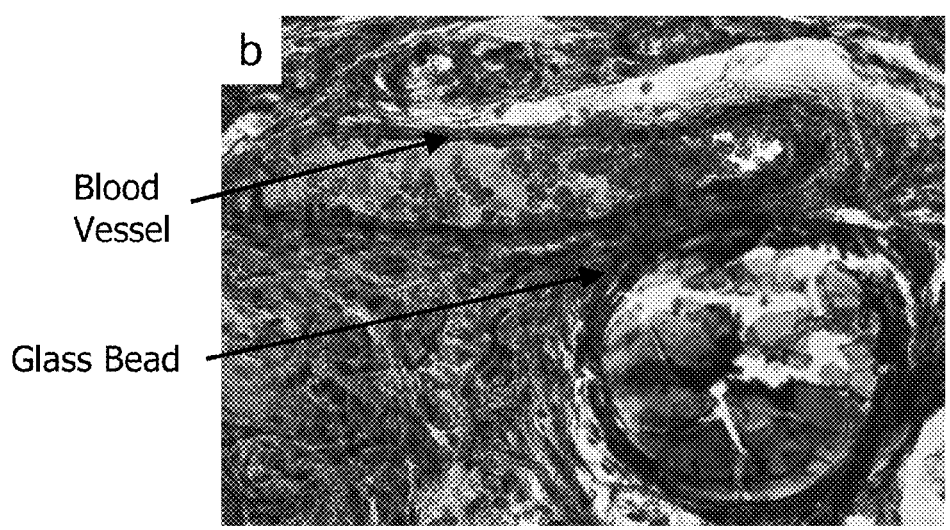
Figure 19:
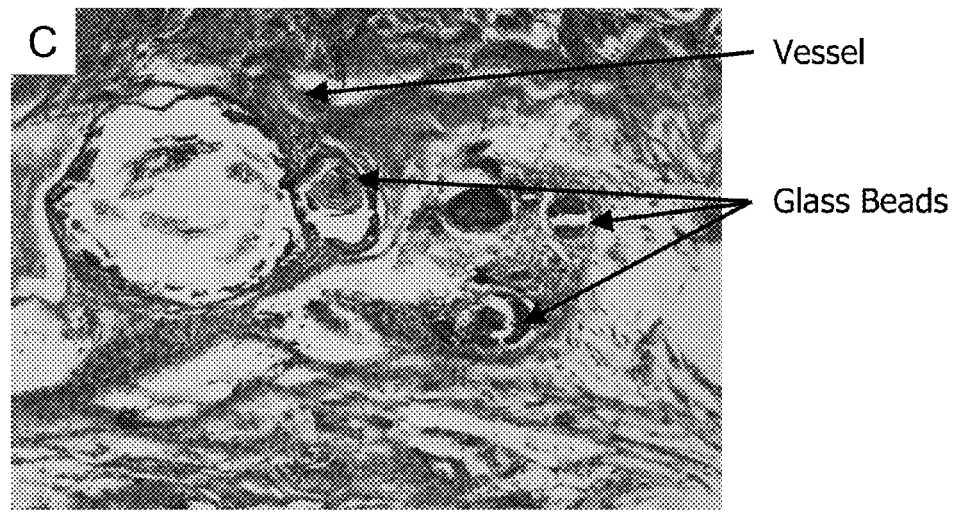
Figure 20:
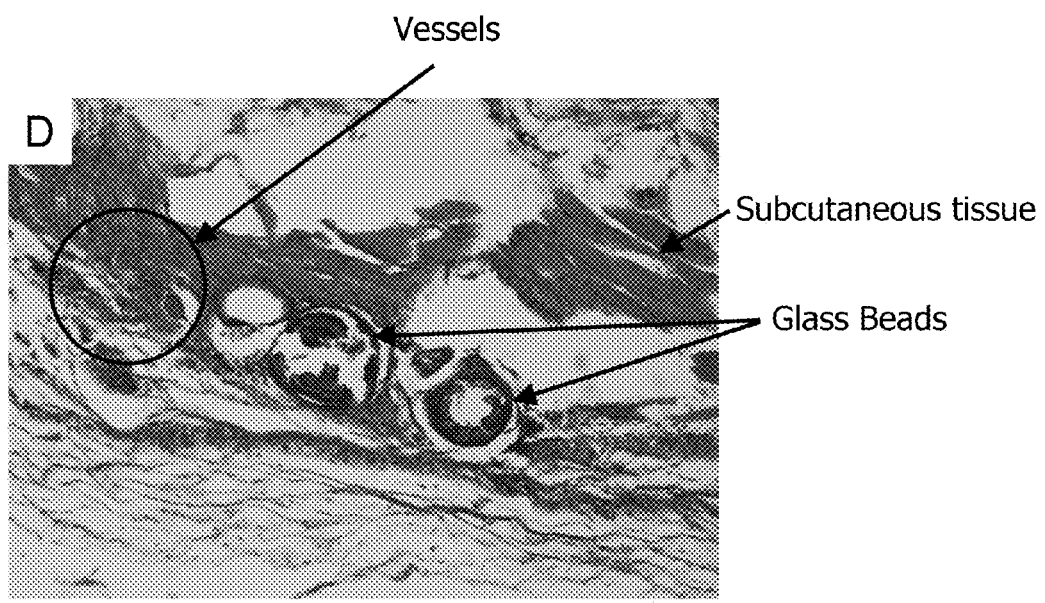

After 22 days, the animals were sacrificed, and the wounds and surrounding tissue was recovered from each animal for histological analysis. FIG. 16 is a representative histological section from the wound covered with dressing. The glass fibers were either dissolved in the body fluids, or removed as the scab peeled away, as they were not visible in these photos. Glass microspheres that had reacted in the animal that were left behind from the dressing are shown in FIGS. 18, 19 and 20. However, the microspheres seen in FIGS. 18 and 19 did act as an indicator of where the fibers were prior to wound closure. The wound dimensions were approximated by the presence of reacted microspheres left behind in the wound. The approximate original wound size (~1 cm in diameter) has been labeled in FIG. 16, and significant healing is evident.

FIGS. 16 through 20 all show glass microspheres that reacted in-vivo to form hollow microspheres of hydroxyapatite. Previous experiments have proven that the glass of the disclosed composition reacts to form hydroxyapatite when placed in an in-vivo environment. FIG. 18 is a magnified view of 17, and a blood vessel is seen adjacent to a reacted glass bead. This vessel appears to be evidence that boron, which is released from the glass as it reacts in-vivo, produced an angiogenic effect in the animal and enhanced the wound healing process. There was also a vessel close to two of the reacted microspheres in FIG. 19 as indicated by the arrow, and there were also three vessels next to the reacted microspheres in FIG. 20 (circled), as indicated by the arrow.

Figure 17:
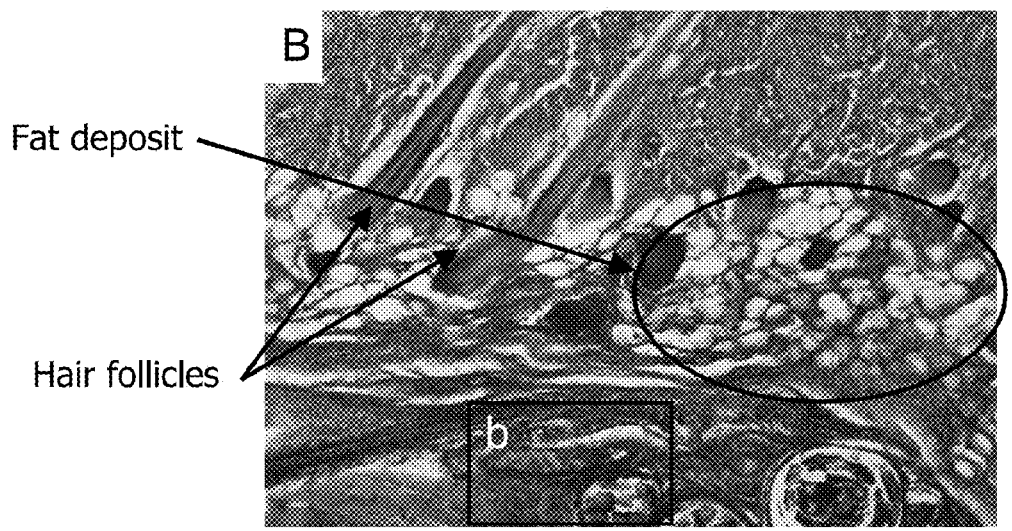

From the histological images present in FIGS. 16 through 20, the tissue that was generated in the presence of the dressing appears similar to the surrounding natural tissue. After 22 days, the dermal and epidermal layers were completely healed, and the subcutaneous tissue (shown in FIG. 20) had almost completely healed as the unhealed section of subcutaneous tissue is indicated by the short horizontal arrow between the two vertical dotted lines in FIG. 16. FIG. 20 shows the subcutaneous tissue that is not completely healed along with some reacted glass bead. There are no visible areas of dead or unhealthy looking tissue, and hair along with fat deposits are present in the regrown tissue similar to the adjacent recovered tissue as shown in FIG. 17.

In view of the above, it will be seen that the several objects of the invention are achieved and other advantageous results attained.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above compositions and methods without departing from the scope of the invention, it is intended that all matter contained in the above description and shown in the accompanying drawings shall be interpreted as illustrative and not in a limiting sense.

The invention claimed is:

1. Glass-based particles of a biocompatible material intermixed into a carrier for angiogenesis in wound-care management,
   wherein the glass-based particles comprise from 40 to about 80 wt % borate ($B_2O_3$);
   wherein the carrier is a biocompatible ointment or cream or a surgical glue for closing a wound; and
   wherein the glass-based particles are angiogenic.

2. The glass-based particles intermixed into a carrier of claim 1, wherein the glass-based particles comprise one or more alkali oxides selected from the group consisting of $Li_2O$, $Na_2O$, $K_2O$, and $Rb_2O$, and one or more alkaline earth oxides selected from the group consisting of MgO, SrO, BaO, and CaO.

3. The glass-based particles intermixed into a carrier of claim 1, wherein the glass-based particles comprise from about 50 to about 80 wt % $B_2O_3$.

4. The glass-based particles intermixed into a carrier of claim 1, wherein the glass-based particles comprise from about 5 to about 20 wt % of one or more alkali oxides selected from the group consisting of $Li_2O$, $Na_2O$, $K_2O$, and $Rb_2O$, and from about 5 to about 40 wt % of one or more alkaline earth oxides selected from the group consisting of MgO, SrO, BaO, and CaO.

5. The glass-based particles intermixed into a carrier of claim 1 wherein the carrier is the biocompatible ointment or cream.

6. The glass-based particles intermixed into a carrier of claim 5 wherein the glass-based particles further comprise one or more trace elements selected from the group consisting of Ag, Cu, F, Fe, Mn, Mo, Ni, Sr, and Zn in a concentration between about 0.05 and 10 wt % per trace element chemically dissolved in glass.

7. The glass-based particles intermixed into a carrier of claim 5 wherein the glass-based particles further comprise Cu in a concentration between about 0.05 and 10 wt % chemically dissolved in the glass.

8. The glass-based particles intermixed into a carrier of claim 6 wherein the one or more trace elements comprise Cu in a concentration which is between 0.1 and 2.5 wt %.

9. The glass-based particles intermixed into a carrier of claim 6 wherein the one or more trace elements comprise 0.05 to 5 wt % Zn.

10. The glass-based particles intermixed into a carrier of claim 5 wherein the glass-based particles comprise from about 50 to about 80 wt % $B_2O_3$, 1 to 25 wt % $Na_2O$, 1 to 25% $K_2O$, 1 to 40 wt % CaO, 1 to 25 wt % MgO, and 1 to 10 wt % $P_2O_5$.

11. The glass-based particles intermixed into a carrier of claim 6 wherein the glass-based particles comprise from about 50 to about 80 wt % $B_2O_3$, 1 to 25 wt % $Li_2O$, and 1 to 40 wt % CaO.

12. The glass-based particles intermixed into a carrier of claim 6 wherein the glass-based particles comprise from about 50 to about 80 wt % $B_2O_3$, 1 to 25 wt % $Na_2O$, and 1 to 40 wt % CaO.

13. The glass-based particles intermixed into a carrier of claim 6 wherein the glass-based particles comprise from about 50 to about 80 wt % $B_2O_3$, 1 to 25 wt % $Na_2O$, and 1 to 40 wt % BaO.

14. The glass-based particles intermixed into a carrier of claim 6 wherein any Ca concentration in the glass-based particles is strictly controlled to less than 0.5 wt %.

15. The glass-based particles intermixed into a carrier of claim 1 wherein the glass-based particles consist essentially of the $B_2O_3$ from 40 to about 80 wt %; two or more alkali oxides selected from the group consisting of $Li_2O$, $Na_2O$, $K_2O$, and $Rb_2O$; and two or more alkaline earth oxides from the group consisting of MgO, SrO, BaO, and CaO; plus Cu as the trace element in the concentration between about 0.05 and 10 wt %.

16. The glass-based particles intermixed into a carrier of claim 1 wherein the carrier is the surgical glue.

17. The glass-based particles intermixed into a carrier of claim 1 wherein the particles have a particle size between about 1 and about 300 µm.

18. The glass-based particles intermixed into a carrier of claim 1 wherein the particles comprise microspheres.

19. The glass-based particles of the biocompatible material intermixed into the carrier for angiogenesis in wound-care management of claim 1, wherein the glass-based particles comprise no silica ($SiO_2$).

20. The glass-based particles of the biocompatible material intermixed into the carrier for angiogenesis in wound-care management of claim 1, wherein the glass-based particles comprise less than 0.1 wt % silica ($SiO_2$).

21. The glass-based particles of the biocompatible material intermixed into the carrier for angiogenesis in wound-care management of claim 1, wherein the glass-based particles comprise silica ($SiO_2$) in a concentration of up to 18 wt %.

22. The glass-based particles intermixed into a carrier of claim 5 wherein the carrier is the biocompatible ointment.

23. The glass-based particles intermixed into a carrier of claim 5 wherein the carrier is the biocompatible cream.

* * * * *

UNITED STATES PATENT AND TRADEMARK OFFICE
CERTIFICATE OF CORRECTION

PATENT NO. : 9,486,554 B2
APPLICATION NO. : 14/028148
DATED : November 8, 2016
INVENTOR(S) : Jung et al.

It is certified that error appears in the above-identified patent and that said Letters Patent is hereby corrected as shown below:

In the Specification

STATEMENT OF GOVERNMENT INTEREST at Column 1, Lines 15-17:
"This invention was made with Government support under Department of the Army contract W81XWH-08-1-7065. The Government may have certain rights in the invention."

Should read:
-- This invention was made with Government support under Department of the Army contract W81XWH-08-1-0765. The Government has certain rights in the invention. --

Signed and Sealed this
Twenty-fourth Day of May, 2022

Katherine Kelly Vidal
*Director of the United States Patent and Trademark Office*